(12) United States Patent
Nakaie et al.

(10) Patent No.: US 9,082,985 B2
(45) Date of Patent: Jul. 14, 2015

(54) ARYLSULFONIC ACID COMPOUND AND USE THEREOF AS ELECTRON-ACCEPTOR MATERIAL

(71) Applicant: NISSAN CHEMICAL INDUSTRIES, LTD., Tokyo (JP)

(72) Inventors: Naoki Nakaie, Funabashi (JP); Takuji Yoshimoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 98 days.

(21) Appl. No.: 13/891,244

(22) Filed: May 10, 2013

(65) Prior Publication Data

US 2013/0240795 A1 Sep. 19, 2013

Related U.S. Application Data

(63) Continuation of application No. 12/864,914, filed as application No. PCT/JP2009/051169 on Jan. 26, 2009, now Pat. No. 8,460,582.

(30) Foreign Application Priority Data

Jan. 29, 2008 (JP) ................................. 2008-017139

(51) Int. Cl.
*H01L 51/00* (2006.01)
*C07C 309/43* (2006.01)
*C09K 11/06* (2006.01)
*H01L 51/50* (2006.01)

(52) U.S. Cl.
CPC .......... *H01L 51/0052* (2013.01); *C07C 309/43* (2013.01); *C09K 11/06* (2013.01); *C09K 2211/1011* (2013.01); *H01L 51/5052* (2013.01)

(58) Field of Classification Search
CPC ..................................................... H01L 51/00
See application file for complete search history.

(56) References Cited

U.S. PATENT DOCUMENTS

| | | | |
|---|---|---|---|
| 4,952,235 A | 8/1990 | Andree et al. | |
| 2005/0035333 A1* | 2/2005 | Gerlach .......... | 252/500 |
| 2008/0029742 A1 | 2/2008 | Yoshimoto et al. | |
| 2011/0195355 A1 | 8/2011 | Nakaie et al. | |

FOREIGN PATENT DOCUMENTS

| | | | |
|---|---|---|---|
| EP | 0 354 329 A1 | 2/1990 | |
| EP | 1 785 413 A1 | 5/2007 | |
| JP | 2-67262 A | 3/1990 | |
| JP | 9-158091 A | 6/1997 | |
| JP | 2002-151272 A | 5/2002 | |
| WO | WO 2006/025342 A1 | 3/2006 | |

OTHER PUBLICATIONS

"International Search Report, dated, Apr. 14, 2009, issued in PCT/JP2009/051169".
Bharathan et al., "Polymer electroluminescent devices processed by inkjet printing: I. Polymer light-emitting logo", Applied Physics Letters, U.S.A., May 25, 1998, vol. 72, No. 21, pp. 2260-2662.
Burroughes et al., "Light-emitting diodes based on conjugated polymers", Nature, the UK, Oct. 11, 1990, vol. 347, pp. 539-541.
Ganzorig et al., "A Lithium Carboxylate Ultrathin film on an Aluminum Cathode for Enhanced Electron Injection in Organic Electroluminescent Devices", Japanese Journal of Applied Physics, 1999, vol. 38, pp. L1348-L1350.
Gustafsson et al., "Flexible light-emitting diodes made from soluble conducting polymers", Nature, the UK, Jun. 11, 1992, vol. 357, pp. 477-479.
Hung et al., "Enhanced electron injection in organic electroluminescence devices using an Al/LIF electrode", Applied Physics Letters, U.S.A., Jan. 13, 1997, vol. 70, No. 2, pp. 152-154.
Kosower et al., "Intramolecular Donor-Acceptor Systems. 10. Multiple Fluorescences from 8-(Phenylamino)-1-naphthalenesulfonates", Journal of American Chemical Society, 1983, 105(20), pp. 6236-6243.
Nakayama et al., "Preparation of α-Quater-, α-Sexi-, and α-Octithiophenes", Heterocycles, 1987, vol. 26, No. 7, pp. 1793-1796.
Nakayama et al., "Preparation of α-Quinque- and α-Septithiophenes and Their Positional Isomers", Heterocycles, 1987, vol. 26, No. 4, pp. 939-942.
Ochi et al., "Preparation of Linear Oligoaniline Derivatives Using Titanium Alkoxide as a Condensing Agent", Bulletin of Chemical Society of Japan, 1994, vol. 67, No. 6, pp. 1749-1752.

(Continued)

*Primary Examiner* — Randy Gulakowski
*Assistant Examiner* — Jeffrey Washville
(74) *Attorney, Agent, or Firm* — Birch, Stewart, Kolasch & Birch, LLP

(57) ABSTRACT

Disclosed is an arylsulfonic acid compound characterized by being represented by formula (1). By using this compound as an electron-acceptor material, highly uniform film formability can be achieved. By using a thin film containing the arylsulfonic acid compound in an OLED device or a PLED device, there can be obtained excellent EL device characteristics such as low driving voltage, high luminous efficiency and long life.

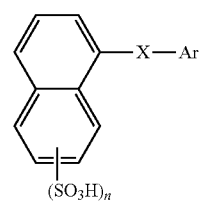

(1)

(In the formula, X represents O, S or NH; Ar represents an aryl group; and n represents the number of sulfonic groups, which is an integer of 1-4.).

20 Claims, 3 Drawing Sheets

(56) References Cited

OTHER PUBLICATIONS

Slyke et al., "Organic electroluminescent devices with improved stability", Applied Physics Letters, U.S.A., Oct. 7, 1996, vol. 69, No. 15, pp. 2160-2162.

Tang et al., "Organic electroluminescent diodes", Applied Physics Letters, U.S.A., Sep. 21, 1987, vol. 51, No. 12, pp. 913-915.

Wakimoto et al., "Organic EL Cells Using Alkaline Metal Comnpounds as Electron Injection Materials", IEEE Transations on Electron Devices, U.S.A., Aug. 1997, vol. 44, No. 8, pp. 1245-1248.

Yang et al., "Polyaniline as a transparent electrode for polymer light-emitting diodes: Lower operating voltage and higher efficiency", Applied Physics Letters, U.S.A., Mar. 7, 1994, vol. 64, No. 10, pp. 1245-1247.

Zhang et al., "Synthesis of Oligomeric Anilines", Synthetic Metals, U.S.A., 1997, vol. 84, pp. 119-120.

Kosower et al., "Intramolecular donor-acceptor systems. 10. Multiple fluorescences from 8-(N-phenylamino)-1-naphthalenesulfonates", Journal of the American Chemical Society, American Chemical Society, Washington, D.C. US, vol. 105, No. 20, Sep. 1, 1983, pp. 6236-6243, XP008138550.

* cited by examiner ness of the materials.
ARYLSULFONIC ACID COMPOUND AND USE THEREOF AS ELECTRON-ACCEPTOR MATERIAL This application is a Continuation of copending application Ser. No. 12/864,914 filed on Jul. 28, 2010, which is a 371 National Phase application of PCT/JP/2009/051169 filed on Jan. 26, 2009, and PCT/JP/2009/051169 claims priority to Application No. 2008-017139 filed in Japan on Jan. 29, 2008. The entire contents of all of the above applications are hereby incorporated by reference.

TECHNICAL FIELD

This invention relates to an arylsulfonic acid compound and the use thereof as an electron acceptor material. For the use, there are mentioned varnishes containing an electron acceptor material consisting of the arylsulfonic acid compound, charge transport thin films using the varnishes, and organic electroluminescent (hereinafter referred to as organic EL) devices using the thin films.

BACKGROUND ART

With regard to organic EL devices, particularly, low molecular weight organic EL (hereinafter abbreviated as OLED) devices, ultrathin film formation of organic layer and functional separation based on multilayering have been promoted by Eastman Kodak Co., thereby significantly improving characteristics of the devices such as a remarkable lowering of drive voltage and the like (Non-Patent Document 1: Applied Physics Letters, U.S.A., 1987, Vol. 51, pp. 913-915).

Devices of organic EL making use of a polymeric luminescent material (hereinafter abbreviated as PLED) have been discovered by Cambridge University (Non-Patent Document 2: Nature, the United Kingdom, 1990, Vol. 347, pp. 539-541). The characteristics of the recent polymeric organic EL devices have been improved to a level not far behind from conventional OLED devices.

As to the OLED devices, it has been reported that when a copper phthalocyanine (CuPC) layer is provided as a hole injection layer, a lowering of drive voltage and improvements of initial characteristics such as an luminous efficiency and a life characteristic can be realized (Non-Patent Document 3: Applied Physics Letters, U.S.A., 1996, Vol. 69, pp. 2160-2162).

On the other hand, it has also been reported that effects similar to those of OLED devices can be obtained when using, as a hole transport layer (buffer layer), polyaniline materials (Non-Patent Document 4: Nature, the United Kingdom, 1992, Vol. 357, pp. 477-479, and Non-Patent Document 5: Applied Physics Letters, U.S.A., 1994, Vol. 64, pp. 1245-1247) and polythiophene materials (Non-Patent Document 6: Applied Physics Letters, U.S.A., 1998, Vol. 72, pp. 2660-2662).

Furthermore, it has been found that initial characteristics are improved when using, as an electron injection layer at the cathode side of these devices, metal oxides (Non-Patent Document 7: IEEE Transactions on Electron Devices, U.S.A., 1997, Vol. 44, pp. 1245-1248), metal halides (Non-Patent Document 8: Applied Physics Letters, U.S.A., 1997, Vol. 70, pp. 152-154), metal complexes (Non-Patent Document 9: Japanese Journal of Applied Physics, 1999, Vol. 38, pp. L1348-1350) and the like. These charge injection layers and buffer layers have now been in ordinary use.

In recent years, an organic solvent-based, charge transport varnish making use of a low molecular weight oligoaniline material has been discovered and it has been found that excellent EL device characteristics are shown by inserting a hole injection layer obtained by use of the above material (Patent Document 1: JP-A 2002-151272).

However, CuPC that is a hole injection material ordinarily used in OLED devices is very irregular in shape, with the attendant drawback that if it is incorporated in other organic layers in very small amounts, characteristics are greatly lowered.

The polyaniline and polythiophene materials currently employed in PLED devices involve problems in that they contain, as a solvent, water that has the possibility of promoting device degradation, limitation is placed on the choice of solvent, and limitation is also placed on the coating method ensuring uniform film formation because of the agglomeration and low solubility of the materials.

Moreover, in case where there is used an organic solvent-based, charge transporting varnish containing a low molecular weight oligoaniline material of high solubility, there may arise problems in that limitation is placed on the kind of usable electron-accepting dopant material and the heat resistance and amorphousness of an electron-accepting dopant are low. Additionally, in an electron transport varnish containing a low molecular weight charge transport material and charge-accepting dopant material, particularly a varnish containing a crystalline material, a difficulty may generally be involved in film formation ensuring high flatness.

Patent Document 1: JP-A 2002-151272
Patent Document 2: WO 2006/025342
Non-Patent Document 1: Applied Physics Letters, U.S.A., 1987, Vol. 51, pp. 913-915
Non-Patent Document 2: Nature, the UK, 1990, Vol. 347, pp. 539-541
Non-Patent Document 3: Applied Physics Letters, U.S.A., 1996, Vol. 69, pp. 2160-2162
Non-Patent Document 4: Nature, the UK, 1992, Vol. 357, pp. 477-479
Non-Patent Document 5: Applied Physics Letters, U.S.A., 1994, Vol. 64, pp. 1245-1247
Non-Patent Document 6: Applied Physics Letters, U.S.A., 1998, Vol. 72, pp. 2660-2662
Non-Patent Document 7: IEEE Transactions on Electron Devices, U.S.A., 1997, Vol. 44, pp. 1245-1248
Non-Patent Document 8: Applied Physics Letters, U.S.A., 1997, Vol. 70, pp. 152-154
Non-Patent Document 9: Japanese Journal of Applied Physics, 1999, Vol. 38, pp. L1348-1350

DISCLOSURE OF THE INVENTION

Problems to be Solved by the Invention

The invention has been made under the circumstances set out above and has for its object the provision of an arylsulfonic acid compound, suited as an electron acceptor material, which is able to realize highly uniform film formability and is also able to realize excellent EL device characteristics such as low drive voltage, high luminous efficiency, long life and the like by application to OLED and PLED devices.

Means for Solving the Problem

We have found and already reported an arylsulfonic acid compound, suited as an electron acceptor material, which is able to realize highly uniform film formability and is also able to realize excellent EL device characteristics such as low drive voltage, high luminous efficiency, long life and the like by application to OLED and PLED devices (Patent Document 2: WO 2006/025342).

Although this arylsulfonic acid compound is soluble in organic solvents, there is still some room of improving the solubility.

Therefore, we made intensive studies and, as a result, found an arylsulfonic acid compound represented by the formula (1), which is excellent in solubility in organic solvents. We have also found that when the above arylsulfonic acid compound is combined with a charge transport host material, the compound accepts the electrons of the charge transport host material and is thus able to improve charge transportability. For this, when the compound is used as a hole injection layer such as of an OLED device or the like, low voltage drive and an improved luminous efficiency are enabled. The invention has been accomplished based on the above finding.

More particularly, the invention provides:
1. An arylsulfonic acid compound, characterized by being represented by the formula (1)

[Chemical Formula 1]

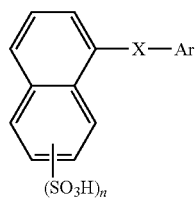

(1)

(wherein X represents O, S or NH, Ar represents an aryl group, and n represents the number of sulfone groups and is an integer of 1 to 4);
2. The arylsulfonic acid compound of 1 represented by the formula (2)

[Chemical Formula 2]

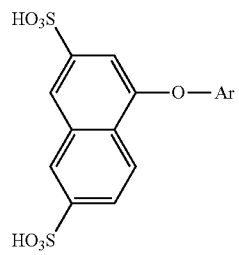

(2)

(wherein Ar represents an aryl group);
3. The arylsulfonic acid compound of 1 or 2, wherein Ar is represented by the following formula (3)

[Chemical Formula 3]

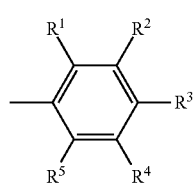

(3)

(wherein $R^1$ to $R^5$ independently represent a hydrogen atom, a halogen atom, an alkyl group having 1 to 10 carbon atoms, a halogenated alkyl group having 1 to 10 carbon atoms, and a halogenated alkenyl group having 2 to 10 carbon atoms);

4. The arylsulfonic acid compound of 3, wherein Ar is represented by the following formula (4)

[Chemical Formula 4]

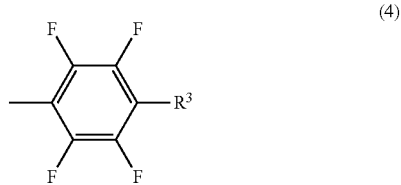

(4)

(wherein $R^3$ represents a hydrogen atom, a halogen atom, an alkyl group having 1 to 10 carbon atoms, a halogenated alkyl group having 1 to 10 carbon atoms, and a halogenated alkenyl group having 2 to 10 carbon atoms);
5. An electron acceptor material consisting of the arylsulfonic acid compound of any one of 1 to 4 above.
6. A charge transport varnish including the electron acceptor material of 5, a charge transport material and a solvent.
7. A charge transport thin film including the electron acceptor material of 5 and a charge transport material.
8. An organic electroluminescent device including the charge transport thin film of 7.

Advantageous Effects

The arylsulfonic acid compound of the invention not only exhibits amorphous solidity at room temperature, but also is high in solubility in various types of organic solvents. Hence, when using an organic solvent-based charge transport varnish containing this compound as a dopant, there can be easily formed an amorphous solid thin film.

Additionally, when the thin film formed as containing the arylsulfonic acid compound of the invention is used as a hole injection layer or hole transport layer, not only the drive voltage of an organic EL device can be lowered and an emission current efficiency can be improved, but also a uniform emission face can be obtained.

Further, the arylsulfonic acid compound of the invention can be employed by use of organic solvents alone, unlike conventionally employed aqueous charge transport varnishes. Thus, device degradation ascribed to moisture incorporation into EL devices can be prevented.

The organic solvent-based charge transport varnish containing the arylsulfonic acid compound of the invention as a charge accepting dopant material can be applied to as protective films for capacitor electrode, antistatic films, ion conducting films and also for use in solar cells, fuel cells and the like.

BEST MODE FOR CARRYING OUT THE INVENTION

Figure 1:
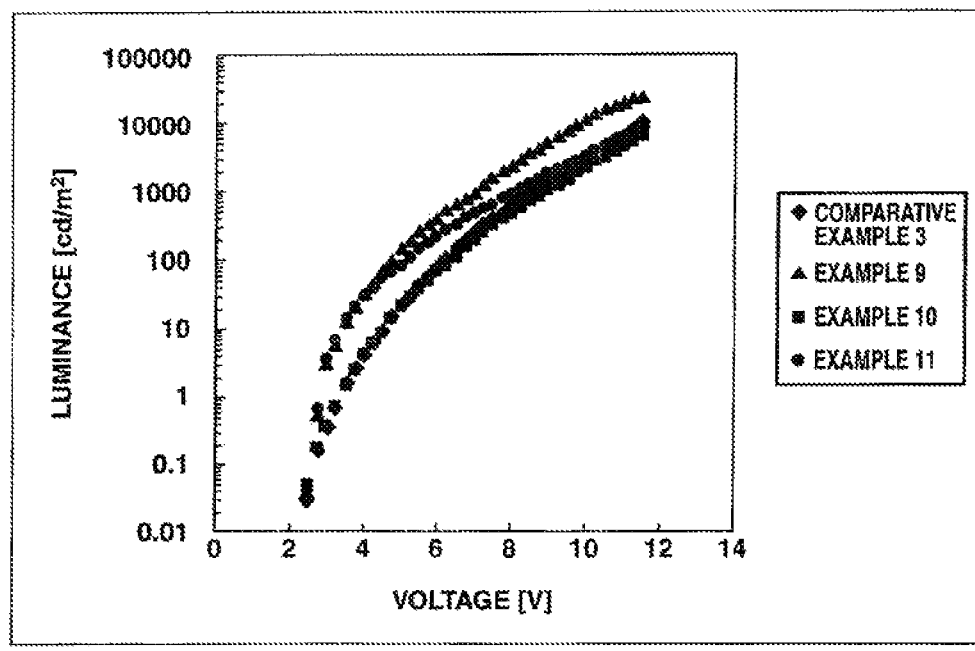
FIG. 1 is a graph showing a voltage-luminance characteristic of OLED devices made in Examples 9 to 11 and Comparative Example 3.

The invention is now described in more detail.

The arylsulfonic acid compound according to the invention is one represented by the formula (1)

[Chemical Formula 5]

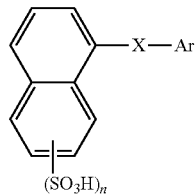

(1)

In the formula (1), X represents O, S or NH, of which O is preferred in view of the ease in synthesis, and n is the number of sulfone groups bonded to the naphthalene ring and is particularly an integer of 1 to 4. In view of the impairment of high electron acceptability and high solubility to the compound, n=1 or 2 is preferred.

Especially, the compound represented by the following formula (2) is preferred.

[Chemical Formula 6]

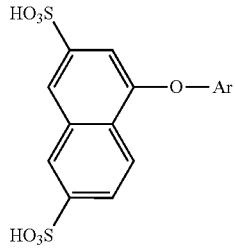

(2)

In the above formulas (1) and (2), Ar represents an aryl group.

As the aryl group, mention is made of those aryl groups including a phenyl group, a xylyl group, a tolyl group, a biphenyl group, a naphthyl group and the like, which may have a substituent.

Examples of the substituent include a hydroxyl group, an amino group, a silanol group, a thiol group, a carboxyl group, a phosphoric group, a phosphoric ester group, an ester group, a thioester group, an amide group, a nitro group, a cyano group, a monovalent hydrocarbon group, an organooxy group, an organoamino group, an organosilyl group, an organothio group, an acyl group, a sulfone group, a halogen atom and the like although not limited thereto.

Specific examples of the monovalent hydrocarbon group include: an alkyl group such as a methyl group, an ethyl group, an n-propyl group, an i-propyl group, an n-butyl group, an i-butyl group, a t-butyl group, an n-hexyl group, an n-octyl group, a 2-ethylhexyl group, a decyl group or the like; a cycloalkyl group such as a cyclopentyl group, a cyclohexyl group or the like; a bicycloalkyl group such as a bicyclohexyl group or the like; an alkenyl group such as a vinyl group, a 1-propenyl group, a 2-propenyl group, an isopropenyl group, a 1-methyl-2-propenyl group, a 1, 2 or 3-butenyl group, a hexenyl group or the like; an aryl group such as a phenyl group, a xylyl group, a tolyl group, a biphenyl group, a naphthyl group or the like; an aralkyl group such as a benzyl group, a phenylethyl group, a phenylcyclohexyl group or the like; and those groups wherein part or all of the hydrogen atoms of the above-mentioned monovalent hydrocarbon groups are substituted with a halogen atom, a hydroxyl group, an alkoxy group, a sulfone group or the like.

Specific examples of the organosilyl group include an alkoxy group, an alkenyloxy group, an aryloxy group and the like, and the alkyl group, alkenyl group and aryl group thereof may be ones similar to those substituent groups mentioned above.

Specific examples of the organoamino group include: an alkylamino group such as a methylamino group, an ethylamino group, a propylamino group, a butylamino group, a pentylamino group, a hexylamino group, a heptylamino group, an octylamino group, a nonylamino group, a decylamino group, a laurylamino group or the like; a dialkylamino group such as a dimethylamino group, a diethylamino group, a dipropylamino group, a dibutylamino group, a dipentylamino group, a dihexylamino group, a diheptylamino group, a dioctylamino group, a dinonylamino group, a didecylamino group or the like; a dicycloalkylamino group such as a cyclohexylamino group or the like; and a morpholino group or the like.

Specific examples of the organosilyl group include a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group and the like.

Specific examples of the organothio group include alkylthio groups such as a methylthio group, an ethylthio group, a propylthio group, a butylthio group, a pentylthio group, a hexylthio group, a heptylthio group, an octylthio group, a nonylthio group, a decylthio group, a laurylthio group and the like.

Specific examples of the acyl group include a formyl group, an acetyl group, a propionyl group, a butyryl group, an isobutyryl group, a valeryl group, an isovaleryl group, a benzoyl group and the like.

The halogen atoms include fluorine, chlorine, bromine and iodine atoms.

The number of carbon atoms of the monovalent hydrocarbon group, organooxy group, organoamino group, organoamino group, organosilyl group, organothio group and acyl group is not limited and is generally at 1 to 20, preferably at 1 to 8.

Among the above-mentioned substituents, the fluorine atom, sulfone group, cyano group, organooxy group, alkyl group and organosilyl group are preferred.

It will be noted that the above-mentioned substituents may contain a cyclic moiety formed by mutual combination of substituents.

In the present invention, the aryl group represented by the following formula (3) is preferably used.

[Chemical Formula 7]

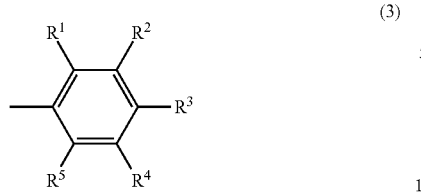

(3)

In the formula, $R^1$ to $R^5$ independently represent a hydrogen atom, a halogen atom, an alkyl group having 1 to 10 carbon atoms, a halogenated alkyl group having 1 to 10 carbon atoms or a halogenated alkenyl group having 2 to 10 carbon atoms.

The halogen atom may be any of chlorine, bromine, fluorine and iodine atoms and is preferably a fluorine atom in the invention.

The alkyl group having 1 to 10 carbon atoms includes a methyl group, an ethyl group, an n-propyl group, an i-propyl group, an n-butyl group, an i-butyl group, a t-butyl group, an n-pentyl group, an n-hexyl group, an n-heptyl group, an n-octyl group, an n-nonyl group, a 2-ethylhexyl group, an n-decyl group, a cyclopentyl group, a cyclohexyl group or the like.

The halogenated alkyl group having 1 to 10 carbon atoms includes a trifluoromethyl group,
a 2,2,2-trifluoroethyl group,
a 1,1,2,2,2-pentafluoroethyl group,
a 3,3,3-trifluoropropyl group,
a 2,2,3,3,3-pentafluoropropyl group,
a 1,1,2,2,3,3,3-heptafluoropropyl group,
a 4,4,4-trifluorobutyl group,
a 3,3,4,4,4-petnafluorobutyl group,
a 2,2,3,3,4,4,4-heptafluorobutyl group,
a 1,1,2,2,3,3,4,4,4-nonafluorobutyl group or the like.

The halogenated alkenyl group having 2 to 10 carbon atoms include a perfluorovinyl group, a perfluoropropenyl group (allyl group), a perfluorobutenyl group or the like.

Of these, the aryl group especially represented by the following formula (4) is preferred in view of the fact that solubility in organic solvent is more enhanced.

[Chemical Formula 8]

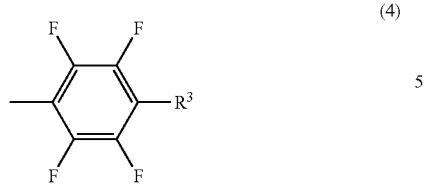

(4)

In the formula, $R^3$ is same as indicated above and represents a hydrogen atom, a halogen atom, an alkyl group having 1 to 10 carbon atoms, a halogenated alkyl group having 1 to 10 carbon atoms or a halogenated alkenyl group having 2 to 10 carbon atoms, of which the halogenated alkyl group and halogenated alkenyl group are preferred. More preferably, a trifluoromethyl group and a perfluoropropenyl group are mentioned.

The method of preparing the arylsulfonic acid compound represented by the formula (1) is not critical and may be appropriately selected from hitherto known various techniques.

For instance, the compound can be obtained by reacting a reagent capable of yielding such an aryl group as mentioned above with the XH group of a naphthalenesulfonic acid compound represented by the following formula (5). The manner of the reaction is not critical and an ordinary nucleophilic substitution reaction may be used, for example.

[Chemical Formula 9]

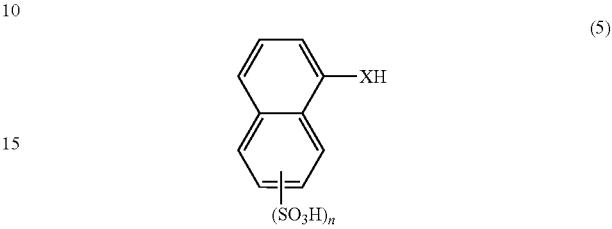

(5)

As such a reagent, there are mentioned aromatic (aryl) compound substituted with a halogen atom such as perfluorobenzene, perfluorotoluene, 3-(pentafluorophenyl)pentafluoro-1-propene, perfluorobiphenyl, octafluoronaphthalene, perfluorobutylbenzene, perfluorophenanthrene, perfluoroacenaphthylene, perfluorofluorene and the like.

Where the arylsulfonic acid compound (5) and the above reagent are reacted with each other, a catalyst may be used.

The catalysts used may be bases such as lithium, potassium, lithium hydride, sodium hydride, lithium t-butoxide, sodium t-butoxide, potassium t-butoxide, lithium-diisopropylamide, n-butyllithium, s-butyllithium, t-butyllithium, lithium hexamethyldisilazide, sodium hexamethyldisilazide, potassium hexamethyldisilazide, lithium hydroxide, sodium hydroxide, potassium hydroxide, barium hydroxide, barium oxide, lithium carbonate, sodium carbonate, potassium carbonate, cesium carbonate, calcium carbonate, sodium hydrogen carbonate, triethylamine, diisopropylethylamine, tetramethylethylenediamine, triethylenediamine, pyridine, dimethylaminopyridine, imidazole and the like, and dehydration condensing agents such as hydrochloric acid, sulfuric acid, diphosphorus pentaoxide, aluminum (III) chloride, boron trifluoride diethyl ether complex, ethyl aluminum dichloride, diethyl aluminum chloride and the like. Of these, it is preferred to use sodium hydride, sodium carbonate and potassium carbonate. The amount of the catalyst is not critical and the catalyst is preferably used in the range of 1.0 to 1.5 times by mole the compound of the formula (5).

The reaction solvent used is preferably an aprotic polar organic solvent and includes, for example, N,N-dimethylformamide, N,N-dimethyacetamide, N-methylpyrrolidone, 1,3-dimethyl-2-imidazolidinone, dimethylsulfoxide, tetrahydrofuran, dioxane and the like. Since solubility of the arylsulfonic acid (5) in an organic solvent is relatively low, it is preferred to use a solvent that has high capability of dissolving the compound and is low in thermal degradability. To this end, 1,3-dimethyl-2-imidazolidinone and N-methylpyrrolidone are preferred among the above-indicated solvents.

The possible reaction temperature generally ranges from −50° C. to the boiling point of a solvent used and is preferably within a range of 0 to 140° C. The reaction time is usually at 0.1 to 100 hours.

After completion of the reaction, purification can be made by distilling off of the reaction solvent, protonation of the sulfonate by means of a cationic exchange resin, extraction operations with a solvent such as methanol or the like, re-precipitation operations, and the like.

It will be noted that the arylsulfonic acid compound of the invention may be obtained according to another synthetic process wherein an aryl compound is subjected to an ordinary sulfonation reaction using concentrated sulfuric acid, fuming sulfuric acid or halo sulfuric acid.

The above-stated arylsulfonic acid compound of the invention has electron acceptability and can be conveniently used as an electron acceptor material.

In the present invention, a charge transport varnish means one wherein at least two materials including a charge transport material acting as a charge transport mechanism body and an electron acceptor material represented by the afore-indicated formula (1) are contained in a solvent. The electron acceptor material is used to improve charge transportability and film formation uniformity and has the same meaning as an electron accepting dopant material.

In the charge transport varnish of the invention, these materials may be either completely dissolved or uniformly dispersed in a solvent.

The charge transportability used herein has the same meaning as conductivity, and also has the same meaning as hole transportability in the invention. The charge transport varnish may have charge transportability in itself, or the solid film obtained from the varnish may have charge transportability.

Although the charge transport material used in the invention is not critical in type so far as there is used a charge transport oligomer or polymer capable of being dissolved or uniformly dispersed in a solvent, it is preferred to use an oligomer having successive conjugated units of one type or an oligomer having a combination of successive conjugated units of different types.

The conjugated unit is not specifically limited so far as it is made of an atom, an aromatic ring or a conjugated group that is able to transport charges. Preferably, mention is made of a substituted or unsubstituted, divalent to tetravalent aniline group, thiophene group, furan group, pyrrole group, ethynylene group, vinylene group, phenylene group, naphthalene group, oxadiazole group, quinoline group, silol group, silicon atom, pyridine group, phenylenevinylene group, fluorene group, carbazole group, triarylamine group, metal or metal-free phthalocyanine group, metal or metal-free porphyrin group or the like.

Specific examples of the substituent include, independently, a hydrogen atom, a halogen atom, a hydroxyl group, an amino group, a silanol group, a thiol group, a carboxyl group, a sulfone group, a phosphoric group, a phosphoric ester group, an ester group, a thioester group, an amide group, a nitro group, a monovalent hydrocarbon group, an organooxy group, an organoamino group, an organosilyl group, an organothio group, an acyl group and the like. These functional groups may be further substituted with any of the above functional groups.

Specific examples of the halogen atom, monovalent hydrocarbon group, organooxy group, organoamino group, organosilyl group, organothio group and acyl group may be those indicated before.

Preferred substituents include a fluorine atom, a sulfone group, and a substituted or unsubstituted organooxy group, alkyl group and organosilyl group. It will be noted that a conjugated chain formed by joining conjugated units may contain a ring moiety.

The number average molecular weight of the charge transport material is preferably at not greater than 5,000 when taking it into account to enhance solubility and at not lower than 200 in order to ensure low volatility and cause charge transportability to be developed. It is preferred to use a material that shows high solubility in at least one type of solvent.

On condition that there is used a material that shows high solubility in at least one type of solvent, the number average molecular weight may range 5,000 to 500,000.

For charge transport material, there is preferably used an oligoaniline derivative set out, particularly, in JP-A 2002-151272. More particularly, the oligoaniline derivative represented by the formula (6) is preferred. It is to be noted that the monovalent hydrocarbon group, organooxy group and acyl group in the following $R^6$-$R^{16}$ represent similar substituents mentioned hereinbefore, respectively.

[Chemical Formula 10]

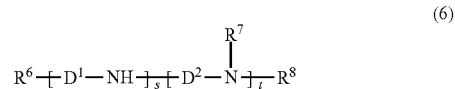

(6)

(wherein $R^6$ represents a hydrogen atom, a monovalent hydrocarbon group or an organooxy group, $R^7$ and $R^8$ independently represent a hydrogen atom or a monovalent hydrocarbon group, $D^1$ and $D^2$ independently represent a divalent group represented by the following formulas (7) and (8).

[Chemical Formula 11]

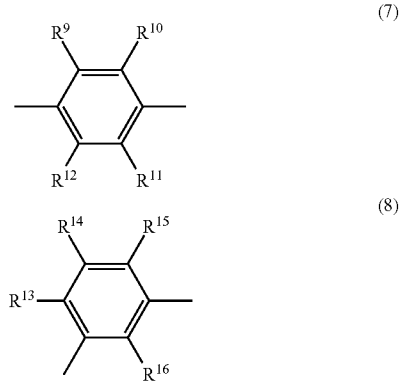

(7)

(8)

$R^9$-$R^{16}$ independently represent a hydrogen atom, a hydroxyl group, a monovalent hydrocarbon group, an organooxy to group, an acyl group or a sulfone group, and s and t are independently an integer of not smaller than 1 provided that s+t≤20 is satisfied).

Furthermore, when the π conjugated system is extended to an extent as great as possible, the resulting charge transport thin film is improved, for which it is preferred to use an oligoaniline derivative represented by the formula (9), or a quinonediimine derivative that is an oxidized product thereof. It will be noted that the substituents designated by like reference numerals in the two benzene rings of the formula (9) may be same or different.

[Chemical Formula 12]

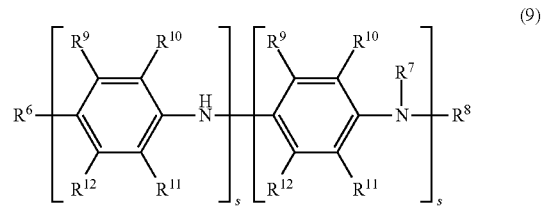

(9)

(wherein $R^6$-$R^{12}$, s and t, respectively, have the same meanings as defined above).

In the formulas (6) and (9), s+t is preferably at 4 or over from the standpoint that good transportability is shown and is at 16 or below from the standpoint that good solubility in solvent is ensured.

Further, the case where $R^6$ is a hydrogen atom and $R^8$ is a phenyl group, or the case where the oligoaniline derivative of the formula (9) is terminated with a phenyl group at opposite ends thereof, is preferred.

These charge transport materials may be used on their own or in combination of two or more.

Specific examples of the compound represented by the above formula (9) include oligoaniline derivatives soluble in organic solvents such as phenyltetraaniline, phenylpentaaniline, tetraaniline (aniline tetramer), octaaniline (aniline octamer) and the like.

The synthetic method of the charge transport material is not critical and includes, for example, synthetic methods of oligoaniline set forth in Bulletin of Chemical Society of Japan, 1994, Vol. 67, pp. 1749-1752 and Synthetic Metals, the U.S.A., 1997, Vol. 84, pp. 119-120 and synthetic methods of oligothiophene set out in Heterocycles, 1987, Vol. 26, pp. 939-942 and Heterocycles, 1987, Vol. 26, pp. 1793-1796.

The mixing ratio of the charge transport material and the arylsulfonic acid compound in the charge transport varnish of the invention is not critical. When improvements of a luminance characteristic and a current density characteristic of the resulting organic EL device is taken into account in case where such an oligoaniline derivative as set out above is used as the charge transport material, the mixing ratio is preferably such that the molar ratio between the nitrogen atom in the charge transport material and the sulfone group in the arylsulfonic acid is preferably at $SO_3H/N=0.1$ to 10, more preferably at 0.5 to 2.

In the charge transport varnish of the invention, a solvent having high dissolution capability and capable of well dissolving a charge transport material and charge acceptor material may be used in an amount of 5 to 10 wt % relative to the total of solvents employed in the varnish. In this case, it is preferred that the charge transport material and charge acceptor material are in a state of being completely dissolved or uniformly dispersed by means of the solvent of high dissolution capability.

The solvent of high dissolution capability is not critical and mention is made, for example, of water, methanol, N,N-dimethylformamide, N,N-dimethylacetamide, N-methylpyrrolidone, 1,3-dimethyl-2-imidazolidinone, dimethylsulfoxide, chloroform, toluene, methanol and the like.

The charge transport varnish of the invention should preferably contain at least one type of organic solvent of high viscosity, which has a viscosity of 10 to 200 mPa·s at 20° C. and a boiling point of 50 to 300° C. at a normal pressure. Moreover, it is also preferred that the charge transport varnish contains an organic solvent that has a viscosity of 50 to 150 mPa·s at 20° C. and a boiling point of 150 to 250° C. at a normal pressure.

The organic solvent of high viscosity is not critical and mention is made, for example, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 1,4-butanediol, propylene glycol, hexylene glycol and the like.

The mixing rate of the organic solvent of high viscosity relative to the total of solvents used in the varnish of the invention is preferably within a range not permitting any solid matter to be precipitated. In so far as no solid matter is precipitated, the mixing rate can be set at 5 to 80 wt %.

It will be noted that for the purposes of improving wettability to substrate and controlling the surface tension, polarity, boiling point and the like of solvent, other type of solvent capable of imparting flatness to a film upon baking may be admixed in an amount of 1 to 90 wt %, preferably 1 to 50 wt %, based on the total of solvents used in the varnish.

Such a solvent is not critical and mention is made, for example, of butyl cellosolve, diethylene glycol diethyl ether, dipropylene glycol monomethyl ether, ethyl carbitol, diacetone alcohol, γ-butyrolactone, ethyl lactate and the like.

The charge transport varnish set forth above can be coated onto a substrate, from which the solvent is evaporated to form a charge transport thin film on the substrate.

The coating method of the varnish is not critical and includes a dipping method, a spin coating method, a spraying method, an ink-jet method, a transfer printing method, a roll coating method, a brushing method and the like. In any of these methods, a uniform film can be formed.

The manner of evaporation of solvent is not critical and the evaporation is carried out by use of a hot plate or an oven in an appropriate atmosphere, i.e., in air or an inert gas such as nitrogen or the like, or in vacuum, by which it is possible to obtain a film having a uniform film-formed surface.

The baking temperature is not critical so far as it enables the solvent to be evaporated and is preferably at 40 to 250° C. In order to develop more uniform film formability and cause the reaction to proceed on the substrate, a temperature change may be made by two or more stages.

The thickness of the charge transport thin film obtained by the coating and evaporation operations is not critical. Where the thin film is applied as a charge injection layer in an organic EL device, the thickness is favorably within 5 to 200 nm. The film thickness can be changed by a method wherein a solid concentration in the varnish is changed or an amount of a coated varnish on a substrate is changed.

The method of making an OLED device using the charge transport varnish of the invention and the materials used therefor are those set out below although not limited thereto.

The electrode substrate used is preliminarily cleaned up by subjecting to liquid cleaning such as with a detergent, an alcohol, pure water or the like. With an anode substrate, it is preferred to subject the substrate to a surface treatment, such as an ozone treatment, an oxygen-plasma treatment or the like, immediately before use. Nevertheless, if an anode material is made primarily of an organic matter, the surface treatment may not be carried out.

Where a hole transport varnish is used for an OLED device, the following method may be adopted, for example.

More particularly, a hole transport varnish is applied onto an anode substrate according to the film-forming method mentioned above to form a hole transport thin film on the electrode. This film is placed in a vacuum deposition apparatus, followed by successive deposition of a hole transport layer, an emission layer, an electron transport layer, an electron injection layer and a cathode metal thereby providing an OLED device. On this occasion, a carrier block layer may be provided between any adjacent layers in order to control an emission region.

As an anode material, mention is made of a transparent electrode material, typical of which is indium tin oxide (ITO) or indium zinc oxide (IZO), and an anode having being subjected to flattening treatment is preferred. Alternatively, polythiophene derivatives and polyanilines having high charge transportability may also be used.

The materials used to form a hole transport layer include triarylamines such as a (triphenylamine)dimer derivative (TPD), (α-naphthyldiphenylamine)dimer (α-NPD), [(triphenylamine)dimer]spirodimer (spiro-TAD) and the like, starburst amines such as 4,4',4"-tris[3-methylphenyl(phenyl)-amino]triphenylamine (m-MTDATA), 4,4',4"-tris[1-naphthyl(phenyl)amino]triphenylamine (1-TNATA) and the like, and oligothiophenes such as 5,5"-bis-{4-[bis(4-methylphenyl)-amino]phenyl}-2,2':5',2"-terthiophene (BMA-3T) and the like.

The materials for forming the emission layer include aluminum (III) tris(8-quinolinolate) (Alq$_3$), zinc (II) bis(8-quinolinolate) (Znq$_2$), bis(2-methyl-8-quinolinolate)-(p-phenylphenolato) aluminum (III) (BAlq), 4,4'-bis(2,2-diphenylbinyl)biphenyl (DPVBi) and the like. It will be noted that the emission layer may be formed by co-deposition of an electron transport material or hole transport material and a light-emitting dopant.

The electron transport materials include Alq$_3$, BAlq, DPVBi, (2-(4-biphenyl)-5-(4-t-butylphenyl)-1,3,4-oxadiazole (PBD), triazole derivatives (TAZ), bathocuproine (BCP), silol derivatives and the like.

The light-emitting dopants include quinacridone, rubrene, coumarin 540, 4-(dicyanomethylene)-2-methyl-6-(p-dimethylaminostyryl)-4H-pyrane (DCM), iridium (III) tris(2-phenylpyridine) (Ir(ppy)$_3$), europium (III) (1,10-phenanthroline)-tris(4,4,4-trifluoro-1-(2-thienyl)-butan-1,3-dionate) (Eu(TTA)$_3$phen) and the like.

The materials for the carrier block layer include PBD, TAZ and BCP.

For the electron injection layer, mention is made of lithium oxide (Li$_2$O), magnesium oxide (MgO), alumina (Al$_2$O$_3$), lithium fluoride (LiF), magnesium fluoride (MgF$_2$), strontium fluoride (SrF$_2$), lithium quinone nolide (Liq), lithium acetylacetonate complex (Li(acac)), lithium acetate, lithium benzoate and the like.

The cathode material includes aluminum, magnesium-silver alloy, aluminum-lithium alloy, lithium, sodium, potassium, cesium or the like.

Where the charge transport varnish of the invention is used as an OLED device, the following method may be adopted.

An electron transport varnish is used to form an electron transport thin film on a cathode substrate and introduced into a vacuum deposition apparatus, followed by forming an electron transport layer, an emission layer, a hole transport layer and a hole injection layer using such materials as set out above, respectively. Thereafter, an anode material is formed as a film by a sputtering or the like method thereby providing an OLED device.

For the fabrication of a PLED device by use of the charge transport varnish of the invention, there may be mentioned the following method although not limited thereto.

In the fabrication of the OLED device set out above, a light-emitting charge transport polymer layer is formed instead of the vacuum deposition operations of the hole transport layer, emission layer, electron transport layer and electron injection layer, thereby enabling the PLED device including the charge transport thin film formed from the charge transport varnish of the invention to be fabricated.

More particularly, the hole transport varnish is coated onto an anode substrate by such a method as mentioned above to form a hole transport thin film on the electrode, on which a light-emitting charge transport polymer layer is formed, followed by vacuum deposition of a cathode electrode to provide a PLED device.

Alternatively, the electron transport varnish may be coated onto a cathode substrate to form an electron transport thin film on the electrode by such a method as mentioned above, on which a light-emitting charge transport polymer material is formed, followed by forming an anode electrode by sputtering, vacuum deposition, spin coating or the like to provide a PLED device.

The cathode and anode materials may be those exemplified with respect to the OLED device, and similar cleaning and surface treatment may be performed.

For the formation of the light-emitting charge transport polymer layer, mention is made of a method wherein a solvent is added to a light-emitting charge transport polymer material with or without addition of a light-emitting dopant to dissolve or uniformly disperse the material in the solvent. The resulting solution is coated onto an electrode substrate on which a hole transport thin film has been formed, followed by evaporation of the solvent to form a film of the material.

The light-emitting charge transport polymer material includes a polyfluorene derivative such as poly(9,9-dialkylfluorene) (PDAF) or the like, a polyphenylenevinylene derivative such as poly(2-methoxy-5-(2'-ethylhexoxy)-1,4-phenylenevinylene (MEH-PPV) or the like, a polythiophene derivative such as poly(3-alkylthiophene) (PAT) or the like, polyvinylcarbazole (PVCz) or the like.

The solvent may be toluene, xylene, chloroform or the like. For dissolution or uniform dispersion, mention is made of a dissolution or uniform dispersion method such as by agitation, agitation under heating, ultrasonic dispersion or the like.

The coating method is not critical, for which mention is made of a dipping method, a spin coating method, a transfer printing method, a roll coating method, a brushing method or the like. The coating is preferably carried out in an inert gas such as nitrogen, argon or the like.

The evaporation of solvent may be carried out by a method of heating with an oven or hot plate in an inert gas or in vacuum.

EXAMPLES

A Synthetic Example, Examples and Comparative Examples are described to more particularly illustrate the invention, which should not be construed as limited to the following Examples.

Synthetic Example 1

Synthesis of Phenyltetraaniline

[Chemical Formula 13]

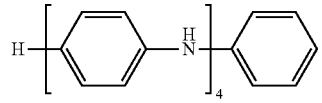

Phenyltetraaniline (PTA) was obtained according to the following procedure based on the method set forth in Bulletin of Chemical Society of Japan, 1994, Vol. 67, pp. 1749-1752.

In 2 liters of toluene, 12.977 g of p-phenylenediamine was dissolved, to which 245.05 g of tetra-n-butoxy titanium serving as a dehydration condensing agent was added, followed by dissolution at 70° C. for 30 minutes. Thereafter, 53.346 g of p-hydroxydiphenylamine was added, followed by reaction at a reaction temperature of 100° C. for 24 hours. After completion of the reaction, the reaction solution was filtered and the resulting filtrate was washed successively with toluene and ether and dried to obtain silver crystals. Then, 25 parts by weight of dioxane and 0.2 equivalents of hydrazine monohydrate, relative to the resulting crystals, were added and the reaction system was purged with nitrogen, followed by heating under reflux to dissolve the crystals. To the resulting solution, 25 parts by weight of toluene relative to the crystals was added to suspend the solution and heated under reflux, followed by further addition of 10 parts by weight of dioxane and heating under reflux for dissolution. The resulting solution was filtered under hot conditions.

The solid precipitated from the filtrate was recrystallized, washed successively with toluene-dioxane (1:1) and ether under nitrogen atmosphere and collected by filtration, followed by drying the resulting crystals under a reduced pressure at 60° C. for 10 hours. Similar recrystallization operations were repeated once more to obtain 39.60 g (yield of 75%) of white crystals.

Example 1

Perfluorotoluene naphthalenesulfonic acid compound (hereinafter abbreviated as 7FNS-1) was synthesized according to the following reaction formula.

[Chemical Formula 14]

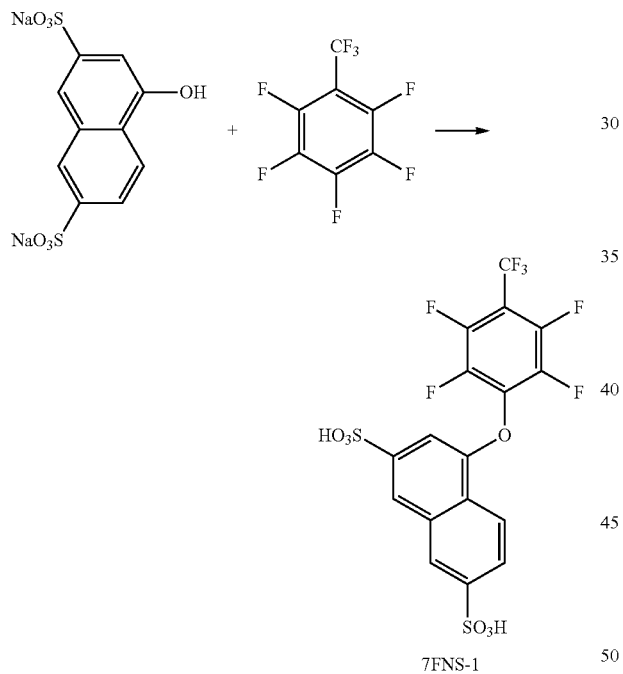

7FNS-1

Under nitrogen atmosphere, 6.78 g of perfluorotoluene, 4.37 g of potassium carbonate and 500 ml of N,N-dimethylformamide were successively added to 10 g of sodium 1-naphthol-3,6-disulfonate (made by Tokyo Chemical Industry Co., Ltd.) and the reaction system was purged with nitrogen, followed by agitation at 100° C. for 5 hours.

After 5 hours, filtration was carried out so as to remove the potassium carbonate. The resultant residue was added with 50 ml of methanol and washed for 30 minutes, followed by filtration of the suspension. The resulting filtrate was concentrated to dryness under reduced pressure, to which 500 ml of pure water was added for dissolution, followed by purification through column chromatography using cationic exchange resin Dowex 650C (about 200 ml of H type, distillate solvent: water).

The fraction whose pH was at 1 or below was concentrated to dryness under reduced pressure to obtain 12.1 g of a white powder (yield: 81%).

Molecular weight: 520.35
MALDI-TOF: 519.0 [M-H]⁻

Example 2

Perfluoroallylbenzene naphthalenesulfonic acid compound (hereinafter abbreviated as 9FNS-1) was synthesized according to the following reaction formula.

[Chemical Formula 15]

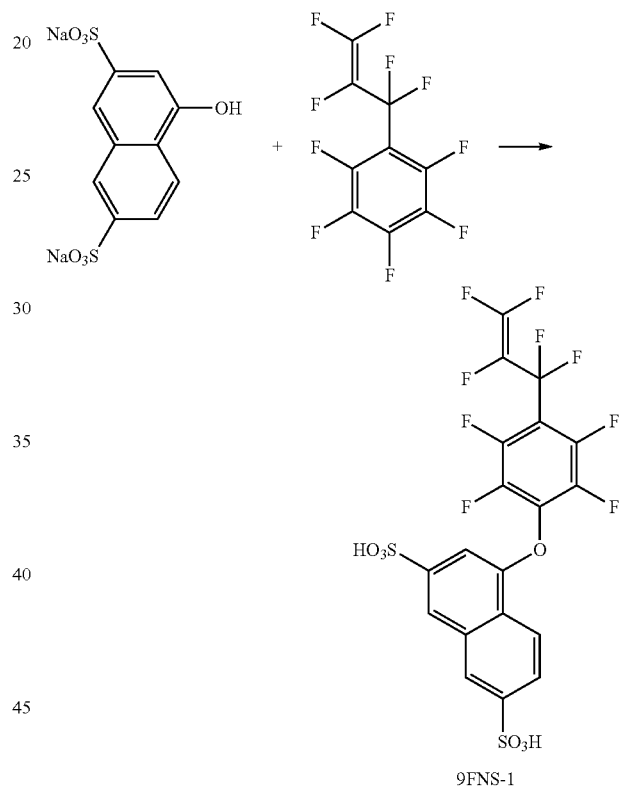

9FNS-1

In the same manner as in Example 1 except that 3.08 g of 3-(pentafluorophenyl)pentafluoro-1-propene, 1.31 g of potassium carbonate and 150 ml of N,N-dimethylformamide were successively added to 3 g of sodium 1-naphthol-3,6-disulfonate (made by Tokyo Chemical Industry Co., Ltd.) and the reaction system was purged with nitrogen, followed by agitation at 100° C. for 5 hours, 3.1 g of a white powder (yield: 62%) was obtained.

Molecular weight: 582.37
MALDI-TOF; 581.0 [M-H]⁻

Example 3

Dicyanoperfluorotoluenesulfonic acid compound (hereinafter abbreviated as 3FNS-1) was synthesized according to the following reaction formula.

[Chemical Formula 16]

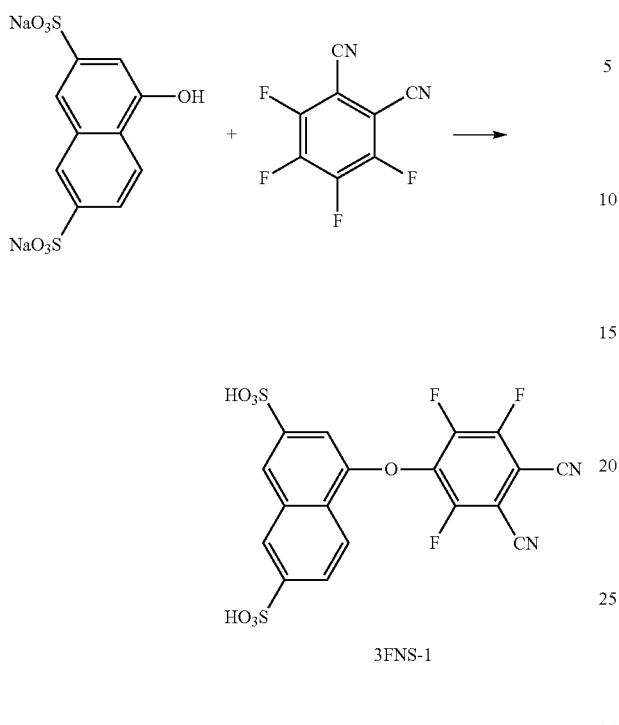

3FNS-1

Under nitrogen atmosphere, 3.38 g of tetrafluorophthalonitrile, 1.87 g of potassium carbonate and 50 ml of N,N-dimethylformamide were successively added to 5 g of sodium 1-naphthol-3,6-disulfonate (made by Tokyo Chemical Industry Co., Ltd.) and the reaction system was purged with nitrogen, followed by agitation at 100° C. for 2 hours.

After 2 hours, 50 ml of DMF was added so as to dissolve a precipitated reaction product therein. Next, filtration was carried out to remove the potassium carbonate. The resulting filtrate was dropped in 200 ml of IPA for re-precipitation. The filtrate obtained by filtration was concentrated to dryness under reduced pressure, to which 50 ml of pure water was added for dissolution, followed by purification through column chromatography using cationic exchange resin Dowex 650C (about 100 ml of H type, distillate solvent: water).

The fraction whose pH was at 1 or below was concentrated to dryness to obtain 5.31 g of a white powder (yield: 97%).

Molecular weight: 484.38
LC-MS: 482.96 [M-H]$^-$

Example 4

Cyanoperfluorotoluenesulfonic acid compound (hereinafter abbreviated as 4FNS-2) was synthesized according to the following reaction formula.

[Chemical Formula 17]

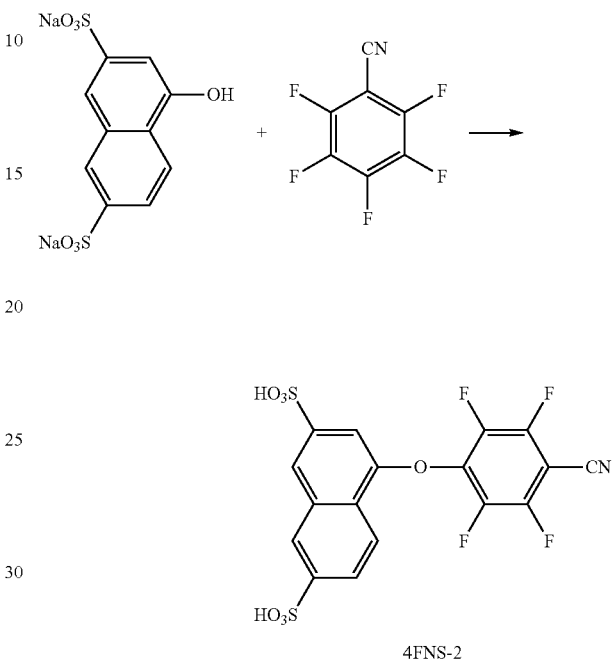

4FNS-2

In the same manner as in Example 3 except that 3.26 g of pentafluorobenzonitrile, 1.87 g of potassium carbonate and 50 ml of N,N-dimethylformamide were successively added to 5.0 g of sodium 1-naphthol-3,6-disulfonate (made by Tokyo Chemical Industry Co., Ltd.) under nitrogen atmosphere and the reaction system was purged with nitrogen, followed by agitation at 100° C. for 2 hours, 5.28 g of a white powder (yield: 98%) was obtained.

Molecular weight: 477.36
LC-MS; 475.95 [M-H]$^-$

Comparative Example 1

Naphthalenedisulfonic acid compound (hereinafter abbreviated as NSO-2) was synthesized according to the following reaction formula.

[Chemical Formula 18]

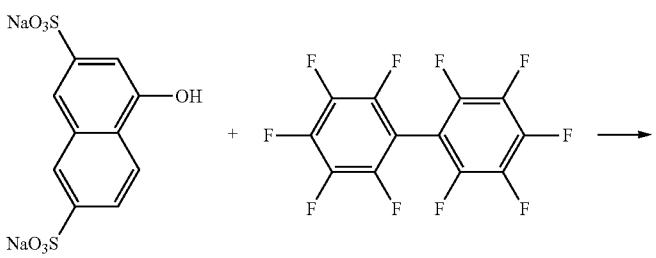

-continued

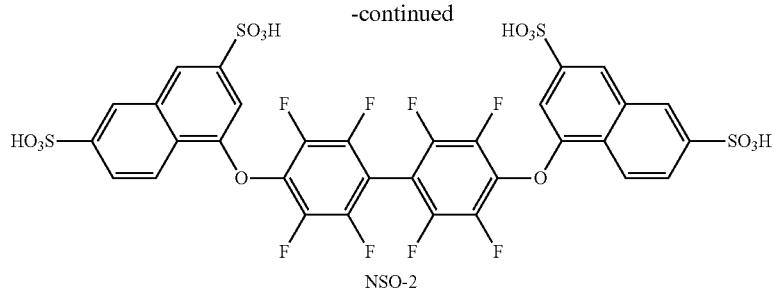

NSO-2

NSO-2 was synthesized according to WO 2006/025342.

Under nitrogen atmosphere, 450 mg of perfluorobiphenyl, 166 mg of 60% sodium hydride and 50 ml of anhydrous N,N-dimethylimidazolidinone were successively added to 934 mg of well dried sodium 1-naphthol-3,6-disulfonic acid (made by Tokyo Chemical Industry Co., Ltd.), and the reaction system was purged with nitrogen and agitated at 80° C. for 43 hours.

After allowing the system to cool down to room temperature, water was added so as to stop the reaction, followed by concentration to dryness under reduced pressure. To the resultant residue, 5 ml of methanol was added and the resulting suspension was added to 100 ml of diethyl ether under agitation. After agitation at room temperature for 1 hour, the precipitated solid was collected by filtration and 25 ml of methanol was added to the filtrate, followed by suspension by application of ultrasonic waves. An insoluble solid was removed by filtration and the filtrate was concentrated to dryness under reduced pressure. To the residue, 12 ml of methanol-water (1:2) was added for dissolution, followed by purification through column chromatography using a cationic exchange resin Dowex 650C (about 40 ml of H type, distillate solvent: methanol-water (1:2)).

The fraction whose pH was 1 or below was concentrated to dryness under reduced pressure, and after subjecting once to azeotropy with isopropanol, 2 ml of isopropanol was added to the residue, followed by addition of the resulting solution to 50 ml of diethyl ether under agitation. After agitation at room temperature for 1 hour, the supernatant liquid was removed and the residue was concentrated to dryness under reduced pressure to obtain 984 mg of a yellow powder (yield of 81%).

[Solubility Test]

The arylsulfonic acid compounds obtained in the above Examples 1 to 4 and Comparative Example 1 were subjected to a solubility test in solvent according to the following procedure. The results are shown in Table 1.

Examples 5 to 8

The respective arylsulfonic acid compounds obtained in Examples 1 to 4 and 0.5 molar equivalents of PTA, relative to the compound, were dissolved in 1 g of 1,3-dimethyl-2-imidazolidinone (hereinafter abbreviated as DMI) so that the solid content was set at 7.0 wt %, thereby preparing varnishes.

Cyclohexanol (hereinafter abbreviated as CHA) was added to the resulting varnish to determine, as an index for solubility, an amount of CHA at the time when the varnish became clouded.

Comparative Example 2

NSO-2 obtained in Comparative Example 1 and 1.0 molar equivalent of PTA, relative to NSO-2, were dissolved in 1 g of DMI so that the solid content was set at 7.0 wt %, thereby preparing a varnish.

CHA was added to the resulting varnish to determine, as an index for solubility, an amount of CHA at the time when the varnish became clouded.

TABLE 1

|  | Arylsulfonic acid compound | Amount of dissolution in CHA (g) |
|---|---|---|
| Comparative Example 2 | NSO-2 | 3.3 |
| Example 5 | 7FNS-1 | >10 |
| Example 6 | 9FNS-1 | >10 |
| Example 7 | 3FNS-1 | 8.0 |
| Example 8 | 4FNS-2 | >10 |

As shown in Table 1, it will be seen that the amounts of dissolution in CHA in Example 5 to 8 are significantly greater than that of Comparative Example 2.

[2] Fabrication of a Low Molecular Weight Electroluminescent (Hereinafter Abbreviated as OLED) Device Comparative Example 3

PTA obtained in Synthetic Example 1 and 0.1 molar equivalent, relative thereto, of NSO-2 obtained in Comparative Example 1 were dissolved in a solvent having mixing ratios of DMI:CHA:propylene glycol (hereinafter abbreviated as PG)=2:3:1 (ratios by weight) so that a solid content was set at 2.8 wt %, thereby preparing a varnish.

This varnish was coated onto an ITO glass substrate by a spin coating method to provide an about 30 nm thick, uniform thin film and introduced into a vacuum deposition apparatus, followed by successively depositing α-NPD, $Alg_3$, LiF and Al to obtain an OLED device. The thicknesses were, respectively, at 30 nm, 50 nm, 1 nm and 120 nm and the vacuum deposition operations were, respectively, performed after the pressure reached $8 \times 10^{-4}$ Pa or below. The deposition rates except for LiF was set at 0.3 to 0.4 nm/second and the rate of LiF was set at 0.02 to 0.04 nm/second. The movement between the deposition operations wad made in vacuum.

Example 9

PTA obtained in Synthetic Example 1 and 2.0 molar equivalents, relative thereto, of 7FNS-1 obtained in Example 1 were dissolved in a solvent having mixing ratios of DMI:CHA:PG=2:3:1 (ratios by weight) so that a solid content was set at 2.8 wt % thereby preparing a varnish.

Using this varnish, a thin film was formed in the same manner as in Comparative Example 3, followed by deposition operations performed in the same manner as in Comparative Example 3 to obtain an OLED device.

Example 10

In the same manner as in Example 9 except that 1.0 molar equivalent of 7FNS-1 obtained in Example 1 was used, an OLED device was obtained.

Example 11

In the same manner as in Example 9 except that 3.0 molar equivalents of 7FNS-1 obtained in Example 1 was used, an OLED device was obtained.

Example 12

PTA obtained in Synthetic Example 1 and 2.0 molar equivalents, relative thereto, of 9FNS-1 obtained in Example 2 were dissolved in a solvent having mixing ratios of DMI: CHA:PG=2:3:1 (ratios by weight) so that a solid content was set at 2.8 wt % thereby preparing a varnish.

Using this varnish, a thin film was formed in the same manner as in Comparative Example 3, followed by deposition operations performed in the same manner as in Comparative Example 3 to obtain an OLED device.

Example 13

In the same manner as in Example 12 except that 1.0 molar equivalent of 9FNS-1 obtained in Example 2 was used, an OLED device was obtained.

Example 14

In the same manner as in Example 12 except that 3.0 molar equivalents of 9FNS-1 obtained in Example 2 was used, an OLED device was obtained.

Example 15

In the same manner as in Example 12 except that 2.0 molar equivalents of 4FNS-2 obtained in Example 4 was used, an OLED device was obtained.

Figure 5:
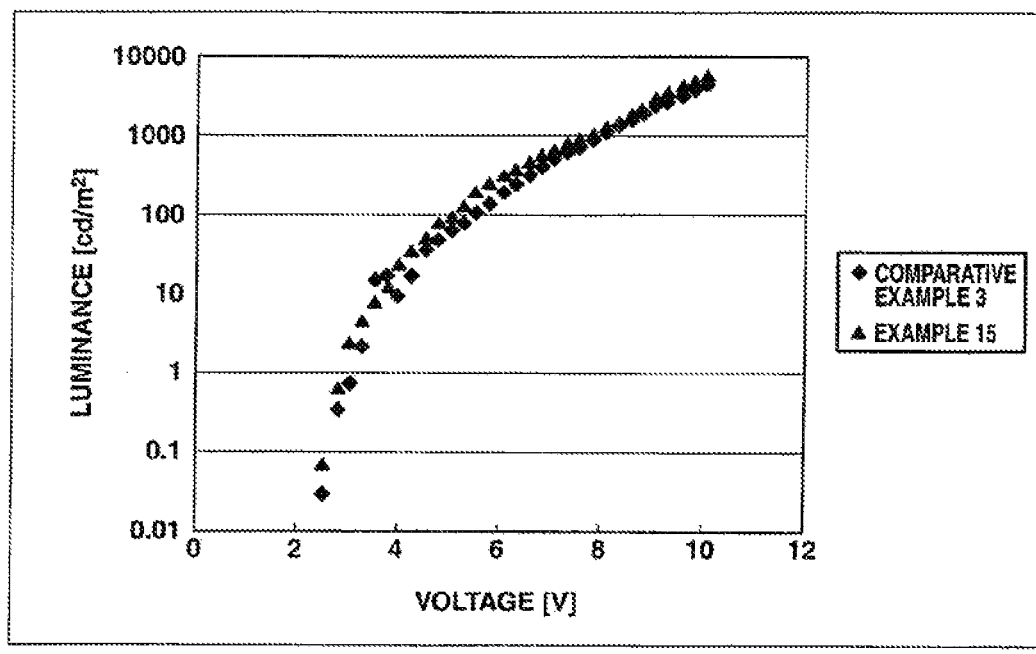
FIG. 5 is a graph showing a voltage-luminance characteristic of OLED devices made in Example 15 and Comparative Example 3.
Figure 6:
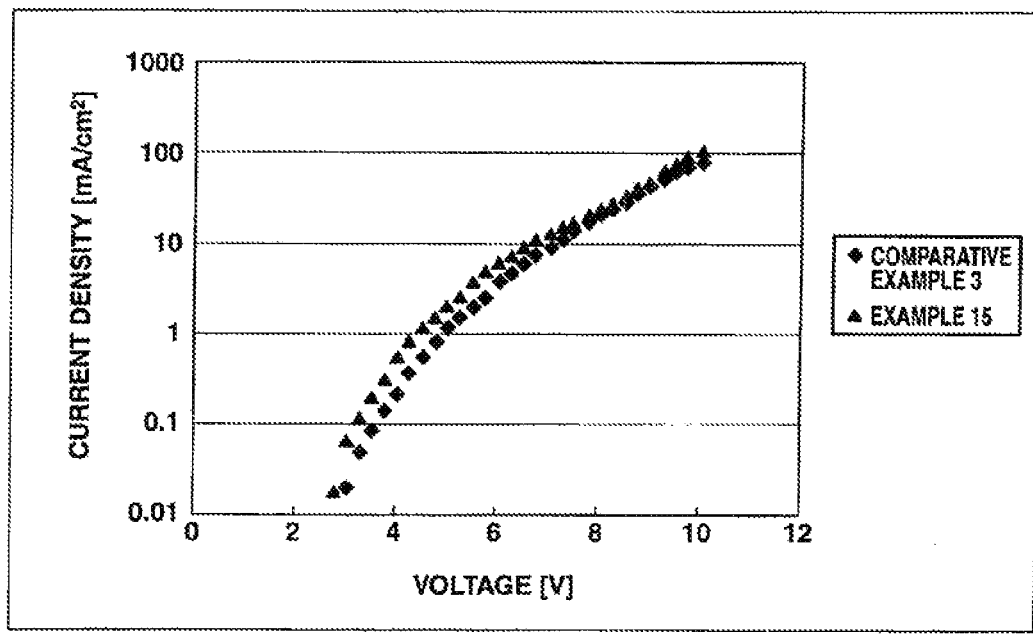
FIG. 6 is a graph showing a voltage-current density characteristic of OLED devices made in Example 15 and Comparative Example 3.

The OLED devices made in the above Examples 9 to 15 and Comparative Example 3 were evaluated with respect to the characteristics thereof. The comparisons between Examples 9 to 11 and Comparative Example 3 are shown in FIGS. 1 and 2, the comparisons between Examples 12 to 14 and Comparative Example 3 are shown in FIGS. 3 and 4, and the comparisons between Example 15 and Comparative Example 3 are shown in FIGS. 5 and 6.

It will be noted that the characteristics of the OLED devices were measured by use of an organic EL luminous efficiency measuring apparatus (EL1003, made by Precise Gauges Co., Ltd.).

Figure 2:
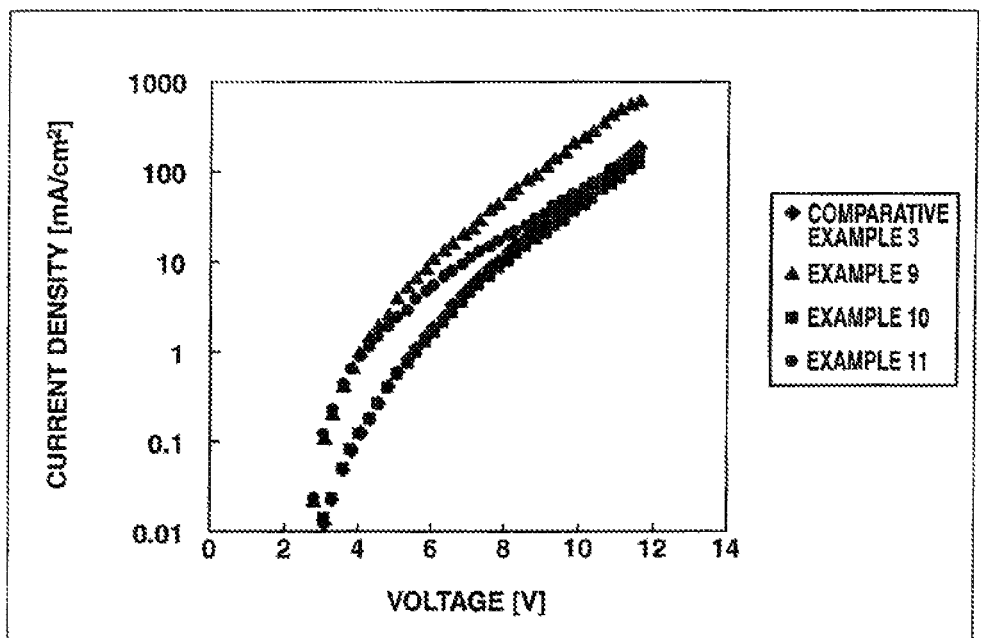
FIG. 2 is a graph showing a voltage-current density characteristic of OLED devices made in Examples 9 to 11 and Comparative Example 3.

As shown in FIGS. 1 and 2, it will be seen that the OLED devices fabricated in Examples 9 and 10 are more excellent in voltage-luminance and voltage-current density than the device of Comparative Example 3. In Example 11, it will also be seen that the luminance and current density are more excellent than those of Comparative Example 3 in a voltage region of 10 V or below.

Figure 3:
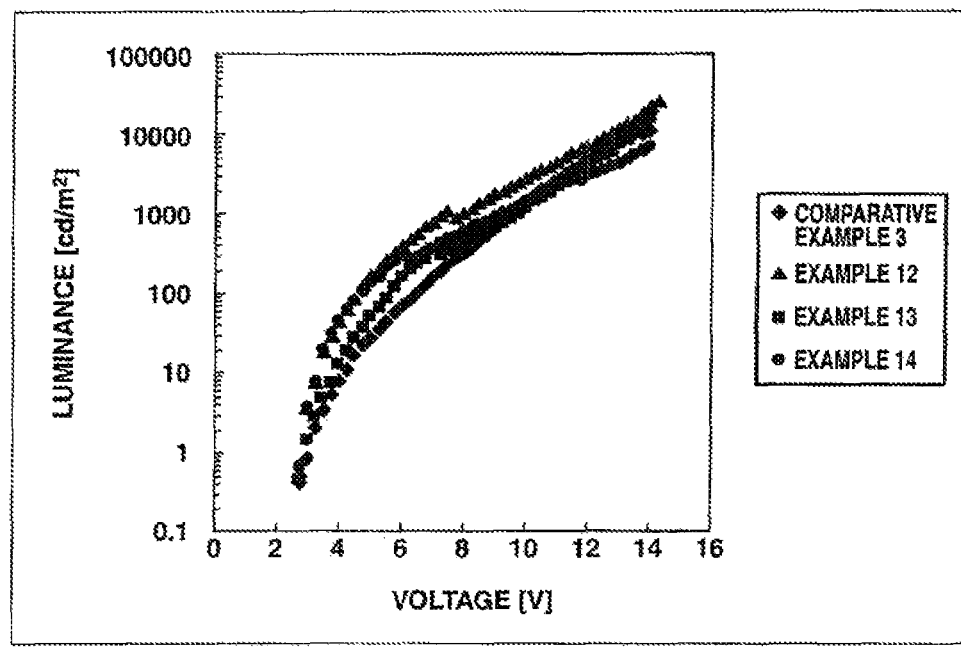
FIG. 3 is a graph showing a voltage-luminance characteristic of OLED devices made in Examples 12 to 14 and Comparative Example 3.
Figure 4:
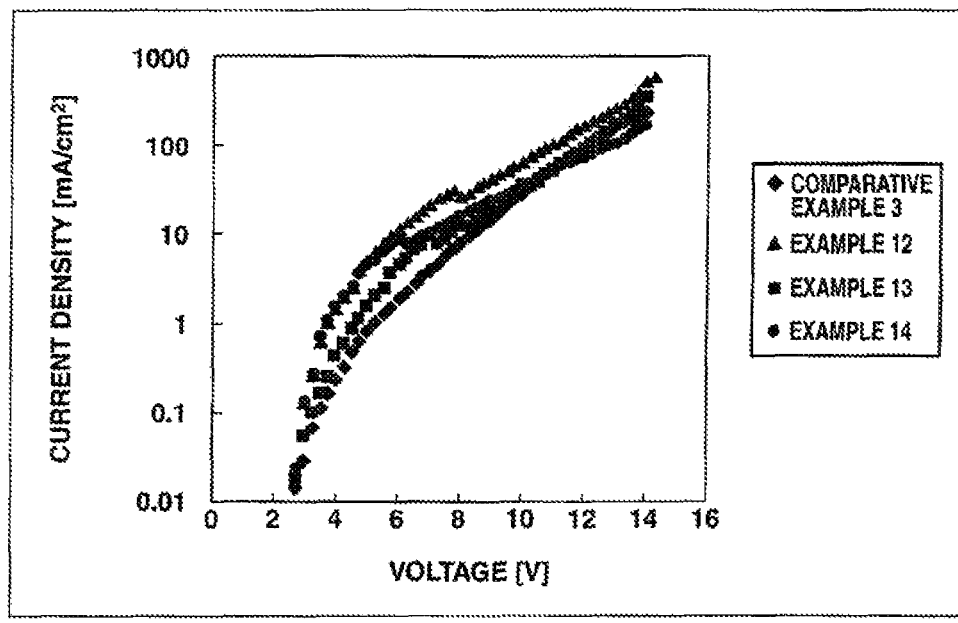
FIG. 4 is a graph showing a voltage-current density characteristic of OLED devices made in Examples 12 to 14 and Comparative Example 3.

As shown in FIGS. 3 and 4, it will be seen that the OLED device made in Example 12 is more excellent in voltage-luminance and voltage-current density than the device of Comparative Example 3. In Examples 13 and 14, it will also be seen that the luminance and current density are more excellent than those of Comparative Example 3 in a voltage region of 10 V or below.

As shown in FIGS. 5 and 6, it will be found that the OLED device made in Example 15 has properties equal to or better than the device of Comparative Example 3.

The invention claimed is:

1. An arylsulfonic acid compound, characterized by being represented by the formula (1)

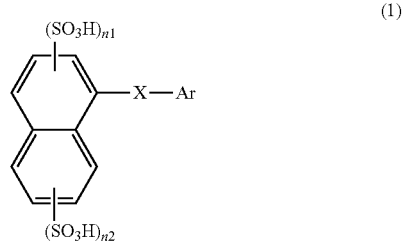

(1)

wherein X represents O, Ar represents a phenyl group directly substituted by fluorine and cyano, and n1 and n2 each independently represent the number of sulfone groups and are an integer of 0 to 2, and satisfy n1+n2=2.

2. The arylsulfonic acid compound according to claim 1, wherein the compound is represented by the formula (2') or (2")

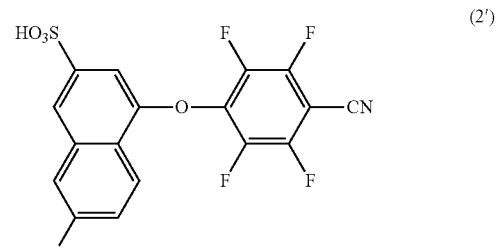

(2')

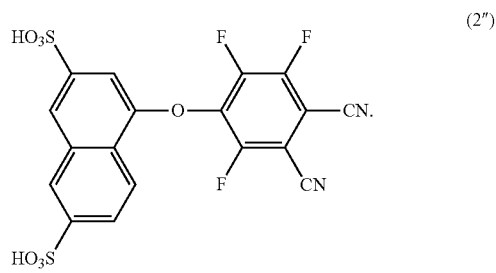

(2")

3. An electron acceptor material consisting of the arylsulfonic acid compound defined in claim 1.

4. A charge transport varnish comprising the electron acceptor material defined in claim 3, a charge transport material and a solvent.

5. A charge transport thin film being obtained from the charge transport varnish defined in claim 4.

6. A charge transport thin film comprising the electron acceptor material defined in claim 3 and a charge transport material.

7. An organic electroluminescent device comprising the charge transport thin film defined in claim 5.

8. The organic electroluminescent device according to claim 7, wherein the charge transport thin film serves as a hole injection layer or a hole transport layer.

9. A method for producing a charge transport thin film, characterized by using the charge transport varnish defined in claim 4.

10. A method for manufacturing an organic electroluminescent device, characterized by using the charge transport thin film defined in claim 5.

11. An electron acceptor material consisting of the arylsulfonic acid compound defined in claim 2.

12. A charge transport varnish comprising the electron acceptor material defined in claim 11, a charge transport material and a solvent.

13. A charge transport thin film being obtained from the charge transport varnish defined in claim 12.

14. A charge transport thin film comprising the electron acceptor material defined in claim 11 and a charge transport material.

15. An organic electroluminescent device comprising the charge transport thin film defined in claim 13.

16. An organic electroluminescent device comprising the charge transport thin film defined in claim 6.

17. An organic electroluminescent device comprising the charge transport thin film defined in claim 14.

18. The organic electroluminescent device according to claim 15, wherein the charge transport thin film serves as a hole injection layer or a hole transport layer.

19. A method for producing a charge transport thin film, characterized by using the charge transport varnish defined in claim 11.

20. A method for manufacturing an organic electroluminescent device, characterized by using the charge transport thin film defined in claim 6.

* * * * *